US00PP24352P3

(12) United States Plant Patent
Bak et al.

(10) Patent No.: US PP24,352 P3
(45) Date of Patent: Mar. 25, 2014

(54) ***VRIESEA* PLANT NAMED 'SPARKLE'**

(50) Latin Name: ***Vriesea* sp.**
Varietal Denomination: SPARKLE

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 113 days.

(21) Appl. No.: 13/506,346

(22) Filed: Apr. 13, 2012

(65) Prior Publication Data

US 2013/0276192 P1 Oct. 17, 2013

(51) Int. Cl.
*A01H 5/00* (2006.01)

(52) U.S. Cl.
USPC ..... Plt./370

(58) Field of Classification Search
USPC ..... Plt./370
See application file for complete search history.

(56) References Cited

U.S. PATENT DOCUMENTS

PP18,176 P3 * 10/2007 Bak et al. ..... Plt./371
PP18,235 P3 * 11/2007 Bak et al. ..... Plt./370
PP22,150 P2 * 9/2011 Bak et al. ..... Plt./370

OTHER PUBLICATIONS

Printout of application information from Community Plant Variety Office (CPVO) website for corresponding CPVO application No. 2011/2618 filed Nov. 3, 2011 (1 page) (http://www.cpvoextranet.cpvo.europa.eu).

* cited by examiner

*Primary Examiner* — Wendy C Haas
(74) *Attorney, Agent, or Firm* — Foley & Lardner LLP

(57) ABSTRACT

A new and distinct *Vriesea* plant named 'SPARKLE' characterized as a funnel form rosette plant, measuring about 35 cm to 40 cm in height (when flowering) and 30 cm to 35 cm in diameter, producing compound, red-orange in color (RHS 34A), bipinate spike inflorescence, measuring about 22-25 cm in height and about 13 cm in diameter, about 5 to 6 branches, and yellow-green foliage, measuring about 18-25 cm in length and about 3.5 cm to 4 cm in width.

1 Drawing Sheet

Latin name of the genus and species of the plant claimed: *Vriesea* sp.

Variety denomination: 'SPARKLE'.

BACKGROUND OF THE INVENTION

The present invention relates to a new and distinct cultivar of *Vriesea* plant, botanically known as *Vriesea* sp., hereinafter referred to by the cultivar name 'SPARKLE'. The genus of *Vriesea* belongs to the Bromeliaceae family.

The new *Vriesea* cultivar is a product of a planned breeding program conducted by—the inventors, Elly Bak and Nico D. M. Steur, in Assendelft, The Netherlands. The objective of the breeding program is to develop a new *Vriesea* variety with good growing habit and attractive inflorescence.

The new *Vriesea* cultivar 'SPARKLE' originated from a cross-made in a controlled breeding program by the inventors in 1998 in Assendelft, The Netherlands. The female or seed parent is a *Vriesea* selection designated '89326' (unpatented). The male or pollen parent is a *Vriesea* selection designated '85249' (unpatented). 'SPARKLE' was discovered and selected by the inventors in May of 2002, as a single flowering plant within the progeny of the stated cross in a controlled environment in Assendelft, The Netherlands.

Asexual reproduction of the new cultivar 'SPARKLE' performed by vegetative means by tissue culture was first performed in 2007, in Assendelft, The Netherlands. The first 'SPARKLE' plants propagated through the use of tissue culture flowered in 2009, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'SPARKLE' which in combination distinguish this *Vriesea* as a new and distinct cultivar:

1. Funnel form rosette plant, measuring about 35-40 cm in total height (when flowering) and 30 cm to 35 cm in diameter;
2. Compound, orange-red (RHS 34A) bipinate spike inflorescence, measuring about 22-25 cm in height, and about 13 cm in diameter.
3. About 5 to 6 branches,
4. Yellow green foliage, measuring 18-25 cm in length and 3.5 cm to 4.0 cm in width.

Plants of the parents, '89326' (unpatented) and '85249' (unpatented), are no longer available to provide a botanical comparison with the new *Vriesea* cultivar 'SPARKLE'. The new cultivar 'SPARKLE' differs primarily from plants of the parental cultivars by exhibiting a more branched inflorescence, orange-red in color.

Of the many commercial cultivars known to the present inventors, the most similar in comparison to the new *Vriesea* cultivar 'SPARKLE' is the *Vriesea* cultivar designated 'STYLE' (U.S. Plant Pat. No. 18,176). Plants of the new cultivar 'SPARKLE' differ from plants of 'STYLE' primarily in inflorescence color.

The new *Vriesea* cultivar 'SPARKLE' can also be compared to the *Vriesea* cultivar designated 'ENERGY' (U.S. Plant Pat. No. 18,235). Plants of the new cultivar 'SPARKLE' differ from plants of 'ENERGY' primarily in that 'SPARKLE' has a higher number of branches.

BRIEF DESCRIPTION OF THE PHOTOGRAPH

The accompanying photograph illustrates the overall appearance of the new *Vriesea* cultivar 'SPARKLE' showing the colors as true as is reasonably possible with colored reproductions of this type. Colors in the photograph may differ slightly from the color values cited in the detailed botanical description which accurately describes the color of 'SPARKLE'.

FIG. 1 shows a side perspective view of a typical potted flowering plant of 'SPARKLE' at about 15 months of age from potting.

DETAILED BOTANICAL DESCRIPTION

'SPARKLE' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Vriesea* cultivar as grown in a greenhouse in Assendelft, The Netherlands, under conditions which closely approximate those generally used in commercial practice. Plants of 'SPARKLE' were grown in a greenhouse with day temperatures ranging from 20° C. to 28° C. and night temperatures ranging from 18° C. to 23° C. No artificial lighting or photoperiodic treatments were conducted, but plants of 'SPARKLE' are forced into flowering by adding acetylene. The following fertilizer is added when growing plants of 'SPARKLE': 1 part nitrogen, 0.6 parts phosphor, 2 parts Kalium and 0.1 parts magnesium.

Color references are made to The Royal Horticultural Society Colour Chart (R.H.S.), except where general colors of ordinary significance are used. Color values were taken under daylight conditions in a greenhouse in Assendelft, The Netherlands. The age of the plants of 'SPARKLE' described is about 15 months from potting.

Classification:
- *Botanical.*—*Vriesea* sp.

Parentage:
- *Male parent.*—*Vriesea* selection designated '89326' (unpatented).
- *Female parent.*—*Vriesea* selection designated '85249' (unpatented).

Propagation: Tissue culture.

Plant:
- *General appearance and form.*—Height: About 35-40 cm (when flowering). Width: About 30-35 cm. Shape: Funnel form rosette.
- *Growth habit.*—Stemless.
- *Plant vigor.*—Good.
- *Flowering season.*—A fully grown plant can flower year round, starting 15 to 17 weeks after induction of natural light or trough flowering treatment.
- *Cold tolerance.*—Frost tender. Temperatures below 5° C. may damage plants.
- *Fragrance.*—None.

Foliage:
- *Quantity.*—About 25 to 30.
- *Size of mature leaf.*—Length: About 18-25 cm. Width: About 3.5-4 cm.
- *Overall shape.*—Broad linear.
- *Apex shape.*—Abruptly acuminate.
- *Base shape.*—Strap-like around central axis.
- *Margin.*—Entire.
- *Texture.*—Smooth and glabrous.
- *Color.*—Leaf color can vary depending on growing conditions. Upper Surface: Mature leaf: Yellow-green, RHS 147A. Immature leaf: Yellow-green, RHS 147B. Lower Surface: Mature leaf: Yellow-green, RHS 147B. Immature leaf: Yellow-green, RHS 147B.
- *Venation.*—None.

Inflorescence:
- *Quantity and form.*—1 flower per floral bract, typical for the genus *Vriesea;* flowering is normally in progression from base to tip of scape.
- *Shape.*—Bipinnate spike (main spike about 12 cm in length and about 5 cm in width, side spike about 10 cm in length and about 4.5 cm in width).
- *Size.*—Height: about 22-25 cm. Diameter: about 13 cm.
- *Color.*—Orange-red RHS 34A. Yellow-orange bract-ends RHS 14A.
- *Corolla.*—Form: Long and narrow, petals and sepals fused at the base around the ovary. Number: About 60-70 depending on the size of the plant.
- *Petals.*—Number: 3 per flower. Length: About 4.5 cm. Width: About 0.6 cm. Overall Shape: Ligulate. Apex Shape: Obtuse. Base Shape: Fused.
- *Color.*—Upper surface: Yellow, RHS 8A. Lower surface: Yellow, RHS 8A.
- *Sepals.*—Number: 3 per flower. Length: About 2.5 cm. Width: About 0.8 cm. Overall Shape: Ligulate. Apex Shape: Acute. Base Shape: Fused. Color: Yellow with little orange-red (as a flush) closest to RHS 13B+RHS 34A.
- *Branches.*—Quantity: About 5 to 6. Length: About 10-12 cm. Width: About 4.5 cm. Color: Orange-red, RHS 34A.
- *Bracts.*—Quantity of bracts on main spike: About 17. Arrangement: Alternate. Size: Length: About 3-4 cm. Width: About 1.5-3 cm. Overall shape: Ovate. Color: Orange red — with yellow bract-ends, RHS 34A+ RHS14A.

Reproductive organs:
- *Androecium.*—Stamen: Number: 6 per flower. Length: About 4.5 cm. Diameter: About 0.1 cm. Color: Yellow, RHS 5D. Anther: Length: About 0.5 cm. Color: Yellow, RHS 5C. Pollen: Amount: Scarce. Color: Yellow, too small to qualify.
- *Gynoecium.*—Pistil: Number: 1 per flower. Length: About 4.5 cm. Stigma: Shape: 3-parted. Width: About 0.3 cm. Color: Yellow-green, RHS 151C. Style: Length: About 4.5 cm. Color: Yellow, RHS 5D. Ovary: Shape: Conical. Length: About 0.8 cm. Diameter: About 0.3 cm. Color: Yellow, RHS 11C.

Disease/pest resistance: No information is currently available.

Disease/pest susceptibility: No information is currently available.

We claim:

1. A new and distinct *Vriesea* plant named 'SPARKLE', substantially as illustrated and described herein.

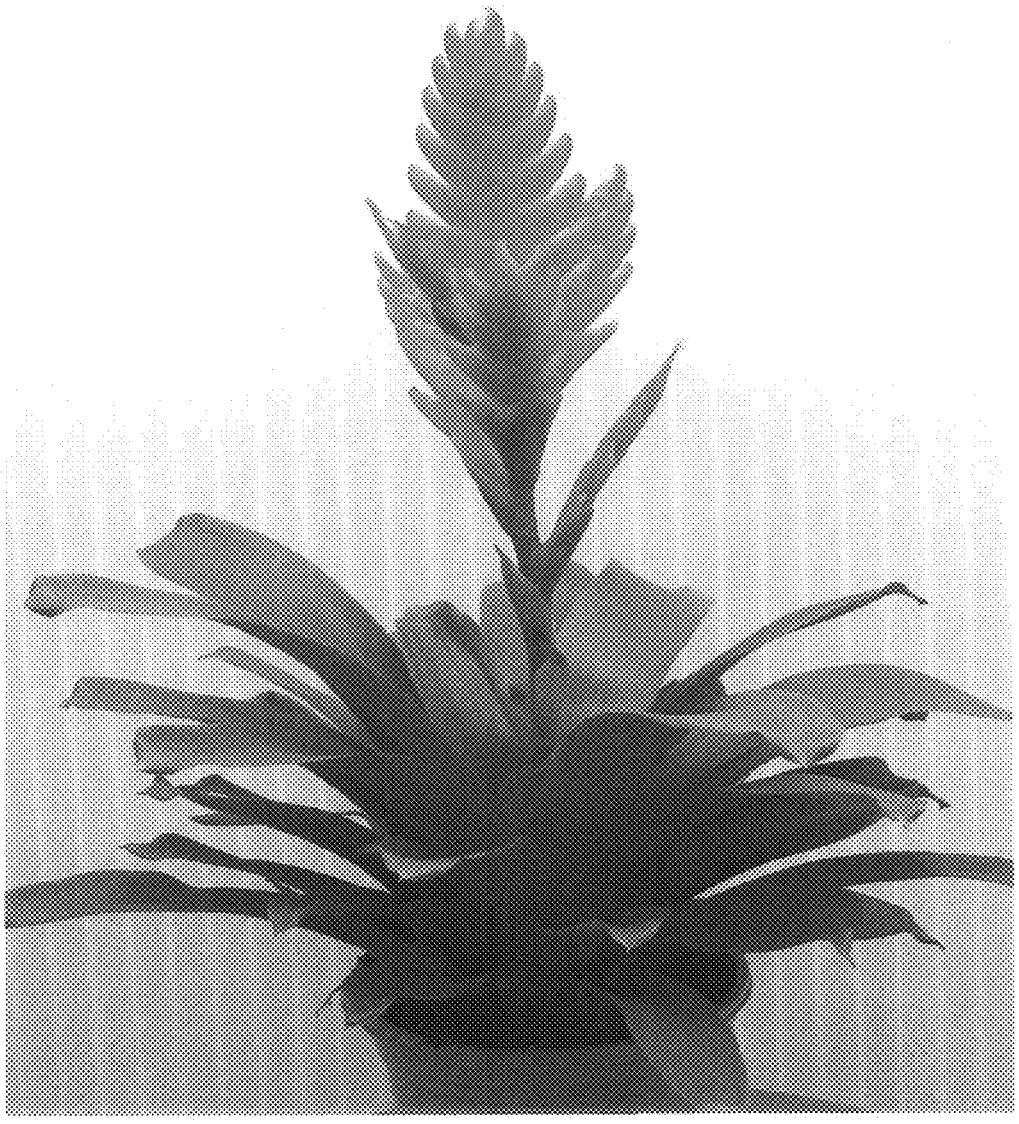

* * * * *